US008690753B2

(12) United States Patent
Stephenson

(10) Patent No.: US 8,690,753 B2
(45) Date of Patent: Apr. 8, 2014

(54) STIMULATION AID

(76) Inventor: Robert Lewis Stephenson, West Midlands (GB)

( * ) Notice: Subject to any disclaimer, the term of this patent is extended or adjusted under 35 U.S.C. 154(b) by 930 days.

(21) Appl. No.: 12/744,944

(22) PCT Filed: Nov. 28, 2008

(86) PCT No.: PCT/GB2008/003949
§ 371 (c)(1), (2), (4) Date: May 27, 2010

(87) PCT Pub. No.: WO2009/068873
PCT Pub. Date: Jun. 4, 2009

(65) Prior Publication Data

US 2010/0305399 A1 Dec. 2, 2010

(30) Foreign Application Priority Data

Nov. 30, 2007 (GB) .................................. 0723648.2

(51) Int. Cl.
*A61F 5/00* (2006.01)

(52) U.S. Cl.
USPC ........................................................ 600/38

(58) Field of Classification Search
USPC ............................ 600/38–41; 601/51, 53, 98
See application file for complete search history.

(56) References Cited

U.S. PATENT DOCUMENTS

| | | | | |
|---|---|---|---|---|
| 3,504,665 | A | 4/1970 | Bakunin et al. | |
| 4,790,296 | A | 12/1988 | Segal | |
| 4,834,075 | A * | 5/1989 | Guo et al. | 601/89 |
| 5,127,396 | A * | 7/1992 | McAllister | 600/38 |
| 5,725,473 | A | 3/1998 | Taylor | |
| 6,142,929 | A | 11/2000 | Padgett | |
| 7,273,460 | B1 | 9/2007 | Nan | |
| 2004/0073146 | A1 | 4/2004 | Weintraub et al. | |
| 2004/0260146 | A1 | 12/2004 | Cao | |
| 2005/0113636 | A1* | 5/2005 | Tucker | 600/38 |
| 2007/0015435 | A1 | 1/2007 | Goudie | |

FOREIGN PATENT DOCUMENTS

| | | | |
|---|---|---|---|
| DE | 32 34 197 | A1 | 6/1983 |
| DE | 20 2004 066 921 | U1 | 9/2004 |
| DE | 20 2004 011 565 | U1 | 11/2004 |
| EP | 1 350 503 | A2 | 10/2003 |
| GB | 2 337 001 | A | 11/1999 |
| GB | 2 403 152 | A | 12/2004 |
| KR | 2002-0067460 | A | 8/2002 |
| NL | 1003501 | C1 | 8/1997 |
| WO | 2005/099366 | A2 | 10/2005 |
| WO | 2007/049830 | A1 | 5/2007 |

OTHER PUBLICATIONS

Knapsack, printed from Internet Archive Wayback Machine, available as of Jul. 22, 2005, 1 page.*

(Continued)

*Primary Examiner* — Samuel Gilbert
(74) *Attorney, Agent, or Firm* — Young & Thompson

(57) ABSTRACT

A stimulation aid includes a housing (8) adapted for retaining against the surface of an individual, the housing having associated therewith retention elements (9) for securing the housing relative to the individual, a power source, drive element and a driven member (11), the driven member being supported for oscillatory motion relative to the housing and, in use, the power source being operable to supply power to the drive element whereby the drive element effects oscillatory motion (x-x) of the driven member.

18 Claims, 5 Drawing Sheets

(56) References Cited

OTHER PUBLICATIONS

International Search Report, dated Feb. 10, 2009, from corresponding PCT application.

British Search Report, dated Mar. 12, 2008, from corresponding British application GB0723648.2.

British Search Report, dated Feb. 27, 2009, from corresponding British application GB0821717.6.

* cited by examiner

STIMULATION AID

BACKGROUND OF THE INVENTION

1. Field of the Invention

This invention relates to a stimulation aid for a human to stimulate a range of sensory experiences. It relates in particular, though not exclusively, to a stimulation aid for assisting an individual to stimulate one of his or her sexual organs.

2. Description of the Related Art

A wide variety of stimulation aids have been proposed, including non-static types which include vibrating or pulsating components. Examples of the latter include those described in, for example, GB 2337001A, KR 20020067460A, EP 1350503A and DE 20 2004006921 U.

Whilst it is understood that the prior known stimulation aids, and particular those of the non-static type, may be effective for undertaking and achieving the desired stimulation effect they do suffer the disadvantage of often being unduly heavy and cumbersome, and in many cases expensive to manufacture and supply.

The present invention seeks to provide an improved stimulation aid which is relatively portable and which overcomes at least some of the disadvantages of prior known stimulation aids.

In accordance with one aspect of the present invention a stimulation aid comprises a housing adapted for retaining against the surface of an individual, said housing having associated therewith retention means for, in use, securing the housing relative to the individual, a power source, drive means and a driven member, said driven member being supported for oscillatory motion relative to the housing and, in use, the power source being operable to supply power to the drive means whereby the drive means effects oscillatory motion of the driven member.

The term "oscillatory motion" is used herein to embrace both linear reciprocal movement of a driven member and also arcuate type movement of a driven member about a pivot position.

The power source and optionally also the drive means may each be substantially wholly contained within the housing, with the driven member extending through a wall of the housing. A distal end of the driven member, external of the housing, may have a stimulation head, such as an elongate or apertured member, e.g. an annular member, associated therewith or may be provided with a connection formation whereby a plurality of different stimulation heads, for example in the form of artificial genitalia, may be selectively fitted to the driven member. It is envisaged that, in use, typically the longitudinal axis of an elongate member or major axis of an orifice or annular member will extend in direction substantially parallel with the general direction of oscillatory movement of the distal end of the driven member.

SUMMARY OF THE INVENTION

It is further envisaged that typically the power source will be a source of electrical energy such as a battery, which may be of the rechargeable type, and that the drive means will be a small D.C. type motor. The motor may be of a type which if necessary incorporates a speed reduction gear or is connected to a reduction gear unit from which torque is transmitted to the driven member. Alternatively, if the motor is of a type having a low rotational speed, a gear unit may be provided to effect a speed increase. More generally, the present invention does not exclude the use of a mechanical type system in which the power source is a mechanical spring and the drive means comprises a mechanical linkage, such as gears, extending between the power source and driven member. In a further alternative the power source may comprise a source of pressurised fluid, such as that of a small, optionally re-chargeable, pressurised gas cylinder, and the drive means may be of a kind operable to convert a flow of pressurised fluid into movement of the driven member. In a yet further alternative the power source may comprise an air compressor.

The housing may be of a substantially sealed type construction and be provided with a switch, such as a pressure operated on-off switch to control the transmission of power from the power source to the drive means. A flexible diaphragm or like member may be provided around the oscillatory driven member to provide a seal with the housing.

The housing may have an electrical connection for recharging of a rechargeable battery which may be located within the sealed housing. Alternatively, and particularly if non-rechargeable batteries are to be employed, a battery compartment may be provided at a position accessible from external of the sealed housing.

In addition to a switch providing a simple control function, such as that of an on-off switch, the stimulation aid optionally may be provided with a speed control, which may be integral with the switch, to vary the speed of operation of the drive means and thus the frequency of the oscillatory motion of the driven member and any stimulator head secured to the distal end of the driven member.

As an alternative to providing the housing with a user interface, such as a surface mounted switch, for control of one or more functions such as the speed of operation of the drive means, the housing may contain a receiver unit to receive signals from a remotely positioned transmitter unit. The transmitter and receiver units may be of a type known per se, such as an infra-red or radio frequency transmitter and receiver. In a further alternative the remote communication may be via or from a transmitter in the form of a mobile phone.

The stimulation aid may comprise a telescopic or otherwise extendable type of driven member whereby the length of the driven member may be varied. Alternatively, and particularly in the case of a stimulator head which is not formed integrally with the driven member, the spacing of a stimulator head from the housing may be varied by selecting a stimulator head of preferred dimensions.

The driven member may comprise electrical conductors for transmission of electrical power from the power source to a stimulator head. Said electrical conductors may be employed for providing electrical power to a stimulation head of a kind which incorporates an electrically powered device such as a heater element or vibrator. In the case of a stimulation head which incorporates a vibrator, and irrespective of whether the vibrator is powered by said conductors or other means such as a battery within the stimulation head, the frequency of operation of the vibrator optionally may be greater than the frequency of oscillatory movement of the driven member.

The housing may incorporate a vibrator device to provide a vibration effect at at least a surface region of the housing which, in use, rests against an individual's body. That vibrator device may be powered by the same power source as that which powers the drive means.

The stimulation aid may comprise a drive means control mechanism which stops the motion of the distal end of the driven member when that end is at a pre-selected or predetermined parking position.

Preferably the drive means is operable to drive the driven member at up to 250 oscillations per minute, more preferably in the range 20 to 200 oscillations per minute. A speed in the range 30 to 150 oscillations per minute is particularly envisaged. Means may be provided for the user to vary the speed within said ranges.

Preferably the drive means is arranged to cause oscillatory movement of the driven member about a pivot position within the housing. Thus the distal end of the driven member, lying external of the housing, will execute an arcuate movement. In this type of configuration the spacing between the stimulator head and housing will enable the arcuate stroke length of the stimulator head to be selectively varied.

One particularly suitable construction comprises a driven member in the form of a pivotally mounted drive arm having an elongate slot which receives a drive pin mounted eccentrically for rotation about the output shaft axis of a motor. The motor may be either of a substantially continuously rotatable type or a servo type motor which is operable to provide continuous oscillatory output rotation through an angle range of less than 360°.

In a construction of the drive means motor and driven member such as that described in the preceding paragraph, and having a driven member pivotally secured relative to the housing, the motor may be movable relative the pivot axis about which the driven member is caused to pivot by the drive means whereby the angle of the arcuate movement of the distal end of the driven member may be varied. Movement may be between pre-established set positions or it may be progressively adjustable to any position within the maximum range of movement. Alternatively or additionally the spacing between the axis of rotation of the motor and an eccentrically mounted drive pin, such as described in the preceding paragraph, may be variable thereby also to vary the angle of arcuate movement of the driven member. Thus the pin may be mounted relative to a motor drive shaft via a spring loaded push and slide switch.

By varying the angle of arcuate movement of the driven member the arcuate stroke length executed by the distal end of the driven member, and thus also an associated stimulation head, may be selectively varied.

In use of the stimulation aid with the stimulation aid held against an individual's body, typically the pelvic region, the force exerted by the oscillating stimulator head on a male or female sexual organ will induce a reactive force between the housing and body. That reactive force may be at a first region of the housing, furthest from the distal end of the driven member when the distal end moves in a first direction, and at a second region of the housing, nearest the distal end of the driven member, when the distal member moves in the opposite direction. This effect may be described as a fore and aft rocking movement.

Optionally the drive mechanism may be designed additionally to create a side to side rocking movement which supplements said fore and aft effect. A side to side rocking movement may be achieved by providing at least a part of the drive for the driven member at a position off-set from the plane in which the outward end region of the driven member oscillates. Alternatively, if a side to side rocking movement is not desired, the drive mechanism may be of a balanced form, having a driven member or plurality of driven members aligned with or balanced relative to said plane in which the output end region of the driven member oscillates.

The retention means for securing the housing relative to a body, and whereby the stimulation aid may be described as a personal type stimulation aid, may be comprised by a belt which is integral with the housing or it may be comprised by one or more retainers for a belt or the like, for example slots through which a belt may be fitted, or a groove into which a belt may be located.

Other forms of retention means envisaged by the present invention include connection means, such as clips, to which the ends of a belt may be secured.

Yet further options for the retention means include a retention surface, preferably a substantially smooth surface and preferably of a kind which is free of sharp protrusions and which, in use, faces outwards from an individual. Said surfaces may be employed, in use of the stimulation aid, to enable the stimulation aid to be retained firmly within a garment extending around the individual or the stimulation aid may be retained in position by hand pressure. That surface may, for example, be textured or provided with means such as a Velcro pad to assist retention of a garment or strap.

The housing may be provided with at least one or, for example, a pair of handle formations. A handle formation may be in the form of a protrusion, such as a solid profiled protrusion, which may readily be gripped by hand. Optionally a part of the protrusion may extend over and be spaced from the surface of the housing thereby to define a recess, groove or aperture which may be employed optionally either as a handle or to locate a belt or other such retainer.

That surface of the housing for resting against the individual preferably is of a contoured non-planar shape, and more particularly preferably is contoured to rest comfortably against the pelvic region. A part of the surface of the housing may be flat and or may be cushioned.

BRIEF DESCRIPTION OF THE DRAWING FIGURES

Embodiments of the present invention will now be described, by way of example only, with reference to the accompanying diagrammatic drawings in which:—

DETAILED DESCRIPTION OF THE INVENTION

Figure 1:
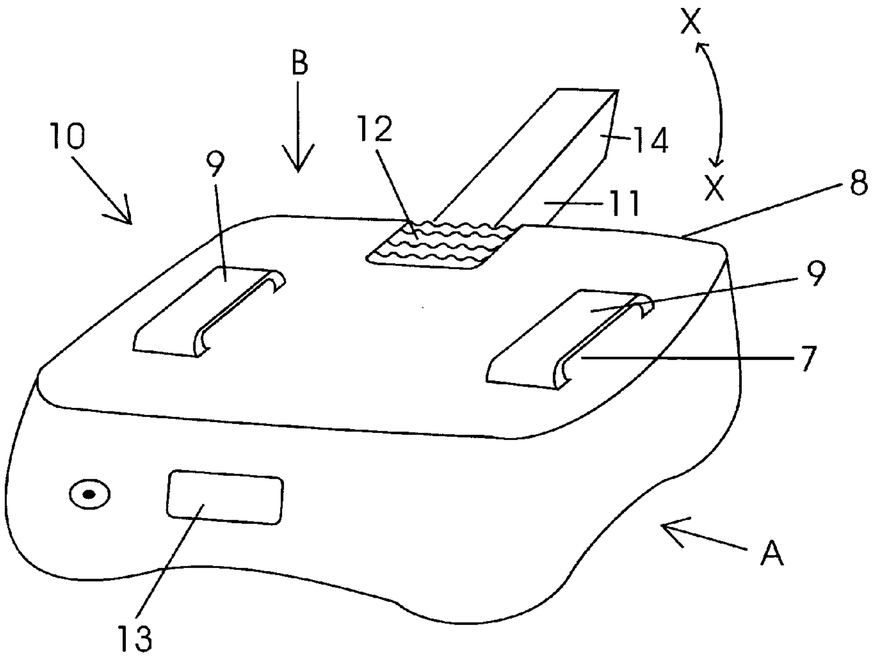
FIG. 1 is a perspective view of a personal stimulation aid in accordance with the present invention.

A personal stimulation aid 10 comprises a sealed housing 8 from which a pivotally mounted drive arm 11 extends for oscillatory motion in the direction XX of FIG. 1. A flexible rubber diaphragm 12 provides a seal between the drive arm 11 and the housing 8. A sealed pressure switch 13 is provided in the wall of the housing for starting and stopping movement of the arm 11.

The upper surface of the housing as viewed in FIG. 1 has a pair of spaced apart band formations 9 which each define a slot 7 through which a belt may be positioned.

Figure 2:
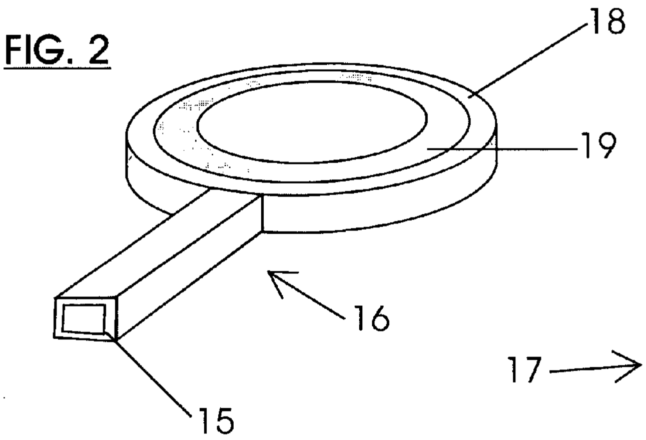
FIG. 2 is a perspective view of an attachment for use with the stimulation aid of FIG. 1.
Figure 3:
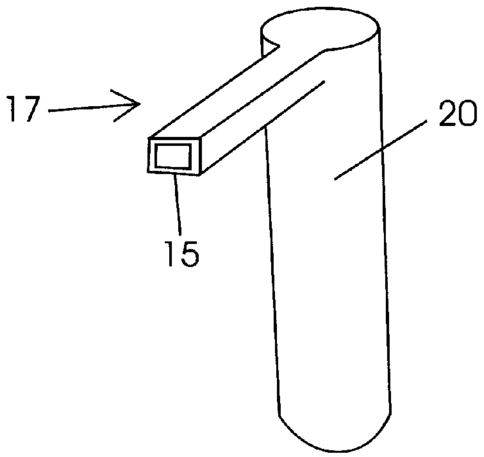
FIG. 3 is a perspective view of another attachment aid for use with the stimulation aid of FIG. 1.

The end region 14 of the arm 11 is slightly tapered to receive, as a friction fit, the tubular shaft 15 of an attachment head 16, 17 such as either of the stimulator head attachments shown in FIGS. 2 and 3.

The attachment 16 of FIG. 2 is designed primarily for male use and comprises an annular plastics support ring 18 which is formed integral with the shaft 15 and which supports within the ring an annular element 19 of a flexible material such as silicone rubber. Other shapes, such as a tubular shape, may be employed.

The attachment 17 of FIG. 3 is designed primarily for female use and comprises a penis like elongate member 20 optionally of substantially rigid or semi-rigid material and which is formed integral with or attached to the tubular shaft 15. Other shapes may be employed, for example a shape representing another part of an individual's anatomy.

The housing 8 (see FIGS. 4 and 5) contains and provides support for a rechargeable battery 25, a dc motor 26 fixed to the housing and a drive mechanism 27 which converts rotary motion of the motor to oscillatory motion of the drive arm 11. Depending on the detailed characteristics of the motor, it may incorporate or be connected to a gear unit which decreases, or alternatively increases, the speed of oscillation of the driven arm. Electrical connections extend between the battery 25 and switch 13 and between the switch 13 and motor 26. Additionally a connection 29 extends between the battery and a socket 28 provided in the wall of the housing for recharging the battery 25.

The drive mechanism comprises a pair of arms 30,31 (see FIG. 4) pivotally mounted about aligned pivot axes 32,33 and inter-connected by a bar 34 from the mid-position of which an outer section of the drive arm 11 extends.

Figure 5:
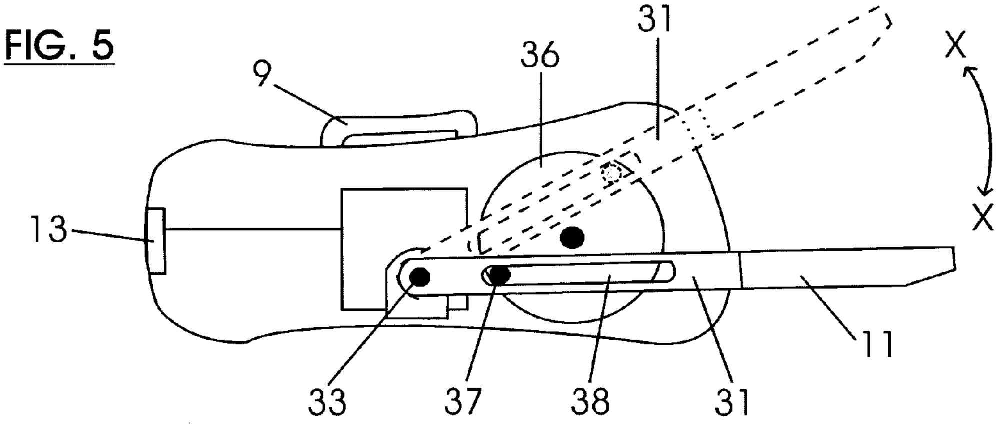
FIG. 5 is an end view in a direction of the arrow A of FIG. 1 with part of the housing cut away.

The motor shaft supports a drive disc 36 provided eccentrically with a pin 37 which engages in a slot 38 in the arm 31 (see FIG. 5). In FIG. 5 the dotted view of arm 31 shows it at a first position of oscillatory movement and the solid view of arm 31 shows it at a second position of oscillatory movement.

In use rotation of the motor causes the pin 37 to induce oscillatory movement to the arm 31, with the pin sliding to and fro along the length of the slot 38. In consequence the distal end of the drive arm 11 executes oscillatory arcuate motion in a plane perpendicular to the axis of rotation of the motor 26.

Figure 4:
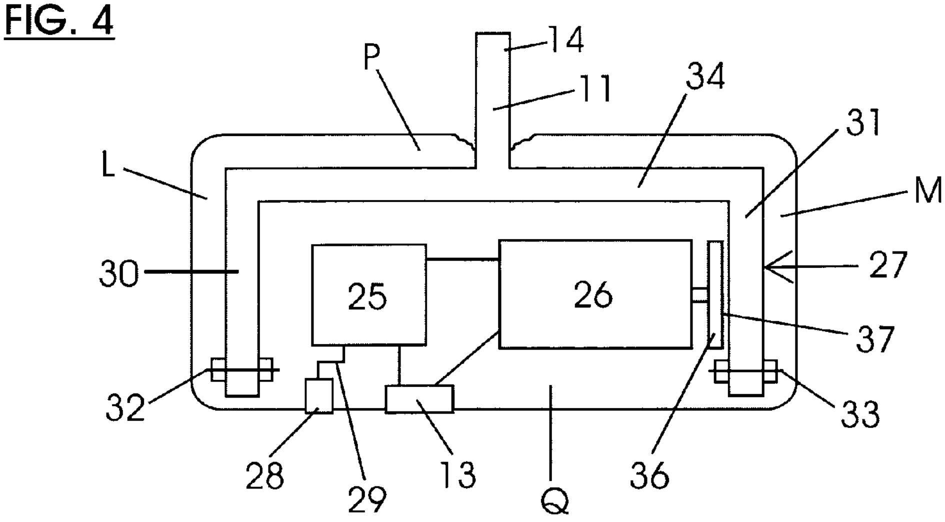
FIG. 4 is a plan view in a direction of the arrow B of FIG. 1 with an upper part of the housing cut away.

In the aforedescribed construction, and with a sufficient degree of free play at the pivot positions 32 and 33, combined with a degree of flexibility of the drive arms 30,31 and interconnecting arm 34, the force exerted by the a stimulator head attached to the drive arm 11 will induce a side to side rocking movement between the base of the housing and body of the user, for example at the regions L and M of FIG. 4 in addition to a fore and aft rocking movement at the regions of the edges P and Q of the housing. However in the alternative construction shown in FIG. 6, a double ended motor shaft is employed to operate two eccentrically mounted pins on the respective discs 40,41 such that each of the driven arms 30' and 31' is driven in a positive manner. In consequence each driven arm has applied thereto a drive force which is substantially balanced about a plane containing the outward section 14' of the driven arm, and extending perpendicular to the axis of rotation of the motor, such that the reactive force experienced in use is confined substantially to a fore and aft rocking movement which is reacted in a vicinity of the respective regions P and Q of the housing, and without a side to side rocking movement.

Figure 6:
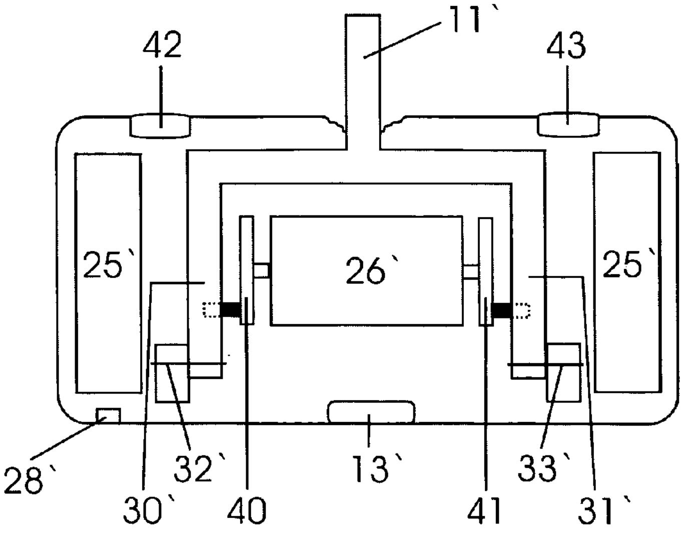
FIG. 6 is a view similar to that of FIG. 4 of a construction in accordance with another embodiment of the present invention.

The stimulation aid of FIG. 6 additionally comprises a pair of vibrator devices 42,43 having vibrator heads which are exposed by apertures in the base region of the housing such that said heads form a part of the housing surface which, in use, will bear against an individual's body.

Figure 7:
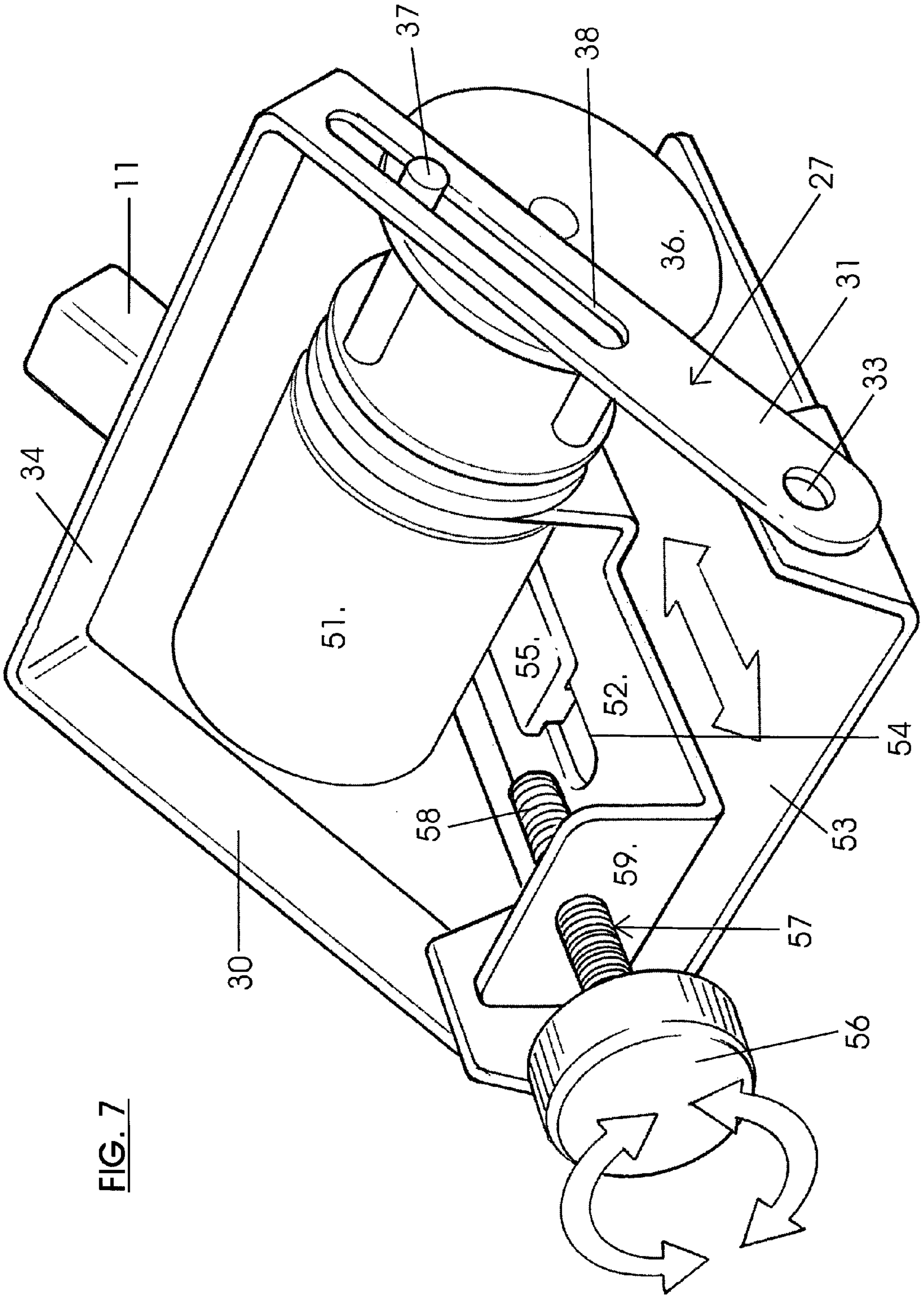
FIGS. 7 to 9 are each perspective views of parts of stimulation aids in accordance with further embodiments of the present invention.

In a third embodiment of the present invention, illustrated in FIG. 7, a stimulation aid 50 is constructed in a manner substantially similar to that of the first embodiment except in respect of the drive mechanism for causing oscillatory movement of the drive arm 11.

Instead of providing a motor 26 which is fixed to the housing, a motor 51 is secured to a carrier 52 which is slidable relative to the housing, in this case via a base plate 53 secured to the housing (not shown). The carrier is provided with a slot 54 which engages with an elongate guide 55 provided on the base plate 53 and oriented such that the motor is guided for sliding movement in a direction perpendicular to the axis of rotation of the motor and the pivot axis 32, 33.

A rotatable knob 56 is provided external of the housing for rotation of a control rod 57 an end region 58 of which is screw threaded for engagement with a screw threaded aperture in an end flange 59 of the carrier 52. A portion (not shown) of the rod 57 between the screw threaded end 58 and knob 50 has a smooth cylindrical surface which is positioned to align with and form a fluid-tight seal with an opening in the housing. A reaction member (not shown) is provided to secure the knob relative to the housing in the direction of the length of the rod 57 whereby, in consequence of the screw thread on the rod engaging that in the flange 59, rotation of the knob results in movement of the carrier 52.

Movement of the motor results in variation of the spacing between the axis of rotation of the drive pin 37 and the pivot axes 32, 33 of the arms 30, 31 and therefore also variation of the arcuate stroke length executed by the distal end of the arm 11.

Figure 8:
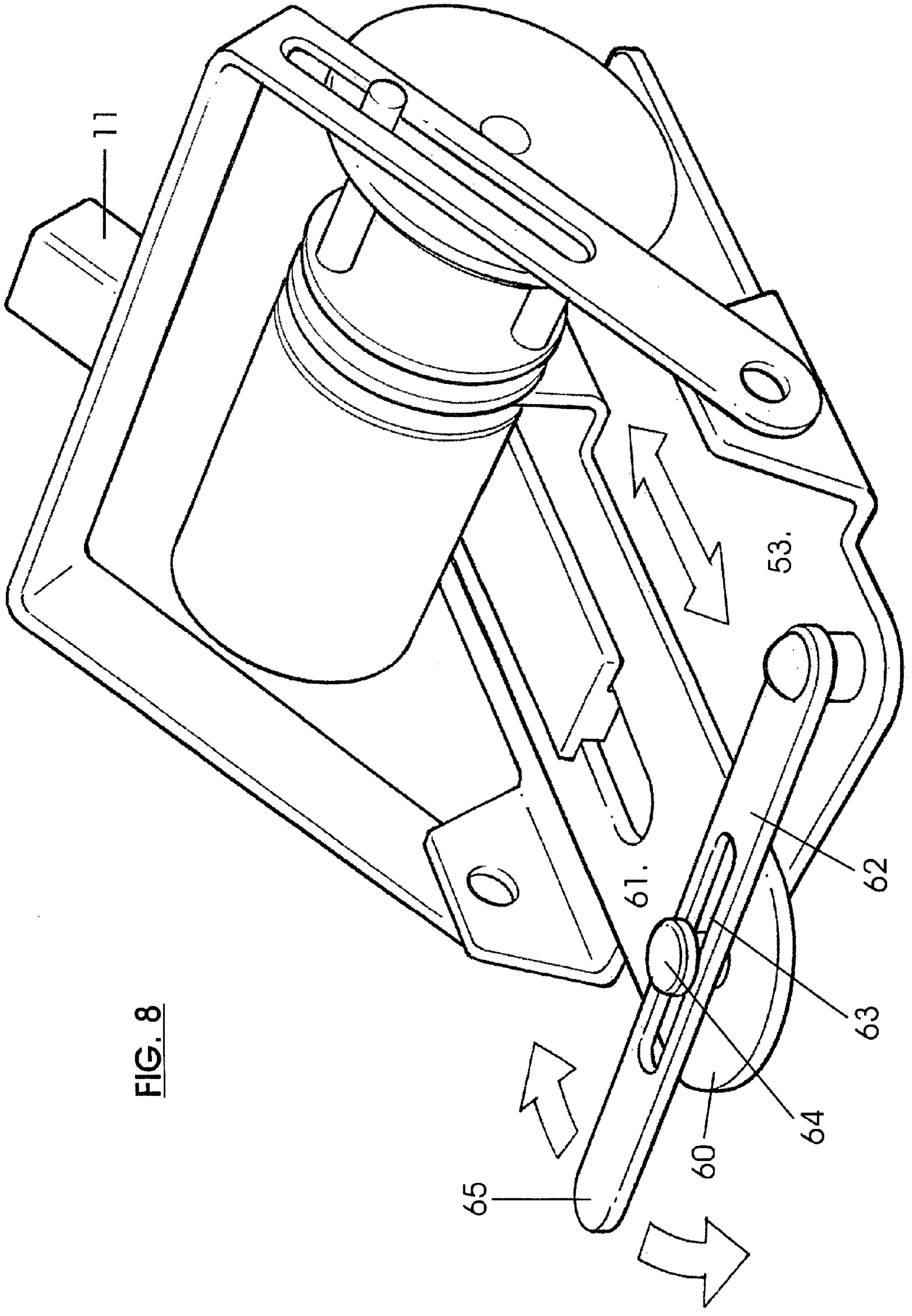

FIG. 8 shows a variation of the construction of FIG. 7. Instead of an apertured flange 59 and rotatable knob 56, an end 60 of the carrier 61 supports a pin 64 which is slidable along a slot 63 in a control arm 62 pivotally secured to the base plate 53. A distal end 65 of the arm 62 may extend through a seal in the housing (not shown) so as to be movable externally of the housing thereby to change the position of the motor and, as described in respect of the preceding embodiment, effect a variation in the arcuate stroke length executed by the distal end of the arm 11.

Figure 9:
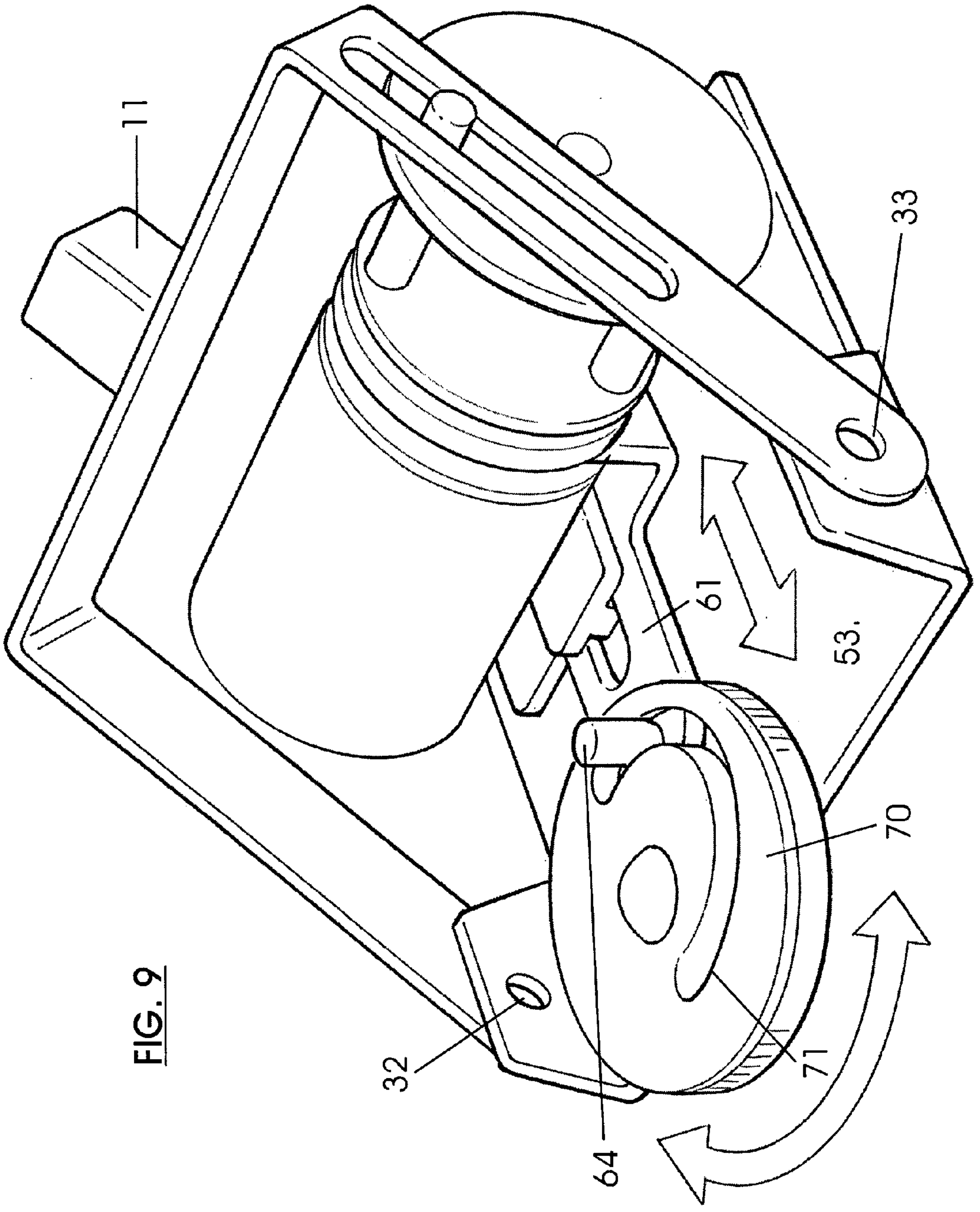

FIG. 9 shows a variation of the construction of FIG. 8. Instead of providing a control arm 62, a cam 70 is rotatably supported by the base plate 53 and is formed with an helically extending slot 71 which engages with the carrier pin 64 such that rotation of the cam results in movement of the carrier 61 thereby to effect a variation in the arcuate stroke length executed by the distal end of arm 11, In the constructions of each of FIGS. 7 to 9 the carrier 61 is caused to move by a means which extends through the housing, typically in a sealed manner, so as to be operable externally of the housing. Alternatively, however, means may be provided for remote operation, for example by means of an infra-red communication link such as that which may also be provided to control on-off operation and rotational speed of the motor.

For the foregoing it will be understood that the present invention provides a stimulation aid which is of a compact construction and which optionally is readily adaptable for both male and female use.

The invention claimed is:

1. A stimulation aid comprising:

a housing adapted for retaining against the surface of an individual, said housing having associated therewith retention means for securing the housing relative to the individual;

a power source;

drive means; and a driven member, said driven member extending outwards from the housing and being supported for oscillatory motion relative to the housing in a direction substantially perpendicular to the direction in which said driven member extends outwards from the housing, said driven member having a distal end which lies external of the housing, said drive means comprising a mechanism for varying the amplitude of oscillatory movement of said distal end of the driven member and, in use, the power source being operable to supply power to the drive means whereby the drive means effects said oscillatory motion of the driven member, wherein the power source and the drive means are substantially wholly contained within the housing, and the driven member extends through a wall of the housing, and wherein a flexible member is provided around the driven member to provide a seal with the housing.

2. A stimulation aid comprising:

a housing adapted for retaining against the surface of an individual, said housing having associated therewith retention means for securing the housing relative to the individual;

a power source;

drive means; and a driven member, said driven member extending outwards from the housing and being supported for oscillatory motion relative to the housing in a direction substantially perpendicular to the direction in which said driven member extends outwards from the housing, said driven member having a distal end which lies external of the housing, said drive means comprising a mechanism for varying the amplitude of oscillatory movement of said distal end of the driven member and, in use, the power source being operable to supply power to the drive means whereby the drive means effects said oscillatory motion of the driven member, wherein the longitudinal axis of a stimulation head in the form of an elongate member or the major axis of a stimulation head in the form of an apertured or annular member extends in a direction substantially parallel with the general direction of oscillatory movement of the distal end of the driven member.

3. The stimulation aid according to claim 2, wherein, in use, the driven member exhibits an arcuate type movement.

4. The stimulation aid according to claim 3, wherein said distal end of the driven member, in use, exhibits an arcuate type movement in said direction substantially perpendicular to the direction in which said driven member extends outwards from the housing.

5. The stimulation aid according to claim 2, wherein the power source and the drive means are substantially wholly contained within the housing, and the driven member extends through a wall of the housing.

6. The stimulation aid according to claim 2, wherein the power source is a battery for providing electrical energy and the drive means comprises a dc type motor.

7. The stimulation aid according to claim 2, wherein the distal end of the driven member comprises a connection formation whereby any one of a plurality of different stimulation heads may be selectively fitted to the driven member.

8. The stimulation aid according to claim 2, further comprising user controllable means to vary the speed of operation of the drive means.

9. The stimulation aid according to claim 2, wherein the drive means provides oscillatory movement of the driven member about a pivot position within the housing and comprises a mechanism for varying the angle of arcuate reciprocal movement of a distal end of the driven member.

10. The stimulation aid according to claim 2, wherein at least a part of the drive means for the driven member is at a position off-set from the plane in which an outward end region of the driven member oscillates.

11. The stimulation aid according to claim 2, wherein the drive means comprises a driven member or plurality of driven members aligned with or balanced relative to the plane in which an outward end region of the driven member oscillates.

12. The stimulation aid according to claim 2, wherein the retention means comprises one of a slot through which a belt may be fitted or a groove into which a belt may be located.

13. The stimulation aid according to claim 2, wherein the retention means comprises a surface which, in use, faces outwards from an individual and may be acted on to enable the stimulation aid to be retained against an individual, and a surface for resting, in use, against an individual and which is of a contoured non-planar shape.

14. The stimulation aid according to claim 2, further comprising a receiver unit to respond to signals from a remotely operable transmitter unit, said receiver and transmitter units being operable to control the speed of oscillation of the driven member.

15. A stimulation aid comprising:

a housing adapted for retaining against the surface of an individual, said housing having associated therewith retention means for securing the housing relative to the individual;

a power source;

drive means; and a driven member, said driven member extending outwards from the housing and being supported for oscillatory motion relative to the housing in a direction substantially perpendicular to the direction in which said driven member extends outwards from the housing, said driven member having a distal end which lies external of the housing, said drive means comprising a mechanism for varying the amplitude of oscillatory movement of said distal end of the driven member and, in use, the power source being operable to supply power to the drive means whereby the drive means effects said oscillatory motion of the driven member, wherein the driven member comprises a pivotally mounted drive arm having an elongate slot which receives a drive pin mounted eccentrically for rotation about the output shaft axis of a motor.

16. The stimulation aid according to claim 15, wherein the spacing between the drive pin and axis of rotation of the motor is selectively variable.

17. The stimulation aid according to claim 15, wherein adjustment means is provided for progressively varying the spacing between the axis of rotation of the motor and the axis about which the drive arm is pivotally mounted, said adjustment means comprising means for moving the motor relative to the housing in a direction perpendicular to the axis of rotation of the motor.

18. A stimulation aid comprising:

a housing adapted for retaining against the surface of an individual, said housing having associated therewith retention means for securing the housing relative to the individual;

a power source;

drive means; and a driven member, said driven member extending outwards from the housing and being supported for oscillatory motion relative to the housing in a direction substantially perpendicular to the direction in which said driven member extends outwards from the housing, said driven member having a distal end which lies external of the housing, said drive means comprising a mechanism for varying the amplitude of oscillatory movement of said distal end of the driven member and, in use, the power source being operable to supply power to the drive means whereby the drive means effects said oscillatory motion of the driven member, wherein the housing contains a vibrator device operable to cause a vibration effect at least a part of the housing which, in use, bears against an individual's body, said vibration device being operable to vibrate at a higher frequency than the frequency of oscillatory movement of the driven member.

* * * * *